(12) United States Patent
Carron et al.

(10) Patent No.: US 7,993,933 B2
(45) Date of Patent: Aug. 9, 2011

(54) CYANIDE AND RELATED SPECIES DETECTION WITH METAL SURFACES

(75) Inventors: Keith T. Carron, Centennial, WY (US); Roberta A. Sulk, Suamico, WI (US); Vince S. Martin, Imperial, CA (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 12/843,997

(22) Filed: Jul. 27, 2010

(65) Prior Publication Data

US 2010/0291701 A1 Nov. 18, 2010

Related U.S. Application Data

(62) Division of application No. 10/840,090, filed on May 6, 2004, now Pat. No. 7,776,610.

(51) Int. Cl.
*B01L 3/00* (2006.01)
(52) U.S. Cl. ........... 436/171; 422/50; 422/430; 436/164
(58) Field of Classification Search .................. 436/171, 436/164; 422/61, 50, 430
See application file for complete search history.

(56) References Cited

U.S. PATENT DOCUMENTS

| | | | |
|---|---|---|---|
| 3,799,742 | A | 3/1974 | Coleman |
| 4,450,231 | A | 5/1984 | Ozkan |
| 4,920,061 | A | 4/1990 | Poynton et al. |
| 5,102,788 | A | 4/1992 | Cole |
| 5,169,789 | A | 12/1992 | Bernstein |
| 5,252,459 | A | 10/1993 | Tarcha et al. |
| 5,255,067 | A | 10/1993 | Carrabba et al. |
| 5,637,508 | A | 6/1997 | Kidwell et al. |
| 5,705,207 | A | 1/1998 | Cook et al. |
| 5,759,774 | A | 6/1998 | Hackett et al. |
| 6,391,652 | B2 | 5/2002 | Okada et al. |
| 6,770,488 | B1 | 8/2004 | Carron et al. |
| 2003/0017620 | A1 | 1/2003 | Carron et al. |
| 2003/0231304 | A1 | 12/2003 | Chan et al. |
| 2004/0135997 | A1 | 7/2004 | Chan et al. |

FOREIGN PATENT DOCUMENTS

WO 9859234 12/1998

OTHER PUBLICATIONS

L. Rivas et al, "Growth of Silver Colloidal Particles Obtained by Citrate Reduction to Increase the Raman Enchancement Factor," Instituto de Estructura de la Materia, CSIC, Serrano 121, E-28006 Madrid, Spain, and Departmento de Quimica Organica y Biologia, Universidad Nacional de Educacion a Distancia, Senda del Rey s/n, E-28040 Madrid, Spain, pp. 574-577, Langmuir 2001.
Kein I. Mullen, Daoxiin Wang, L. Gayle Crane and Keith T. Carron, "Determination of pH with Surface-Enhanced Raman Fiber Optic Probes", Analytical Chemistry, 1992, 64, pp. 930-936.
Roberta Sulk, Collin Chan, Jason Guicheteau, Cieline Gomez, J. B. B. Heyns, Robert Corcoran and Keith T. Carron, "Surface-enhanced Raman Assays (SERA): Measurement of Bilirubin and Salicylate", Journal of Raman Spectroscopy, 1999, 30, pp. 853-829.
P.C. Lee and D. Meisel, "Adsorption and Surface-Enhanced Raman of Dyes on Silver and Gold Sols", American Chemical Society—J. Phys. Chem. 1982, 86, pp. 3391-3395.
G. Ferns, "Controlled Nucleation for the Regulation of the Particle Size in Monodisperse Gold Suspensions", Nature Physical Science, vol. 241, Jan. 1, 1973, pp. 20-22.
Non-Final Office Action dated Nov. 14, 2007 issued in parent U.S. Appl. No. 10/840,090, filed May 6, 2004 of Keith T. Carron.
Final Office Action dated Jul. 30, 2008 issued in parent U.S. Appl. No. 10/840,090, filed May 6, 2004 of Keith T. Carron.
Non-Final Office Action dated Mar. 25, 2009 issued in parent U.S. Appl. No. 10/840,090, filed May 6, 2004 of Keith T. Carron.

*Primary Examiner* — Walter D Griffin
*Assistant Examiner* — Christine T Mui
(74) *Attorney, Agent, or Firm* — Duane Morris LLP

(57) ABSTRACT

An assay method and kit for detecting a chemical. The method and kit utilize a metal surface capable of surface enhanced Raman Scattering. The metal surface may be provided in the form of one or more nanoparticles, to increase the surface enhanced Raman Scattering capability of the metal surface. The nanoparticles may be treated with one or more additives to further enhance or maintain the surface enhanced Raman Scattering capability of the nanoparticles.

15 Claims, 9 Drawing Sheets

US 7,993,933 B2

CYANIDE AND RELATED SPECIES DETECTION WITH METAL SURFACES

RELATED APPLICATIONS

This application is a divisional of U.S. patent application Ser. No. 10/840,090, filed May 6, 2004, which claims the benefit of U.S. Provisional Application No. 60/468,602, filed May 7, 2003. The entire disclosures of U.S. patent application Ser. No. 10/840,090 and U.S. Provisional Application No. 60/418,602 are incorporated herein by reference.

FIELD OF THE INVENTION

The present invention relates to detection and monitoring of chemicals. More particularly, the present invention relates to an assay method and kit for detecting a chemical and/or a species related to the chemical, such as cyanide and its related species, using a metal surface that maintains or produces large enhancements of the Raman scattering (surface enhance Raman Scattering or SERS) when the chemical binds to the metal surface.

BACKGROUND OF THE INVENTION

An assay is defined as a test that identifies a chemical species, determines its presence, and can measure the amount of chemical specie present. The chemical specie is termed an "analyte" in the field of chemical analysis. These assays are relevant to many diagnostic situations.

Cyanide and some of the related species represent a class of very toxic substances. Cyanide and some of the related species are used for a class of compounds known as chemical warfare agents. It would be particularly valuable to be able to detect these chemical warfare agents at concentrations well below the toxic level in order to provide an early warning to potentially affected populations. Cyanide and related species also find widespread use in the mining and chemical manufacturing industries.

The SERS affect stems from an electromagnetic and often chemical enhancement of Raman scattering at a metal surface. Most often the metal surface is composed of silver or gold. These metals produce strong enhancements only under special conditions. One of these conditions is the size of the metal surface. A common method of performing SERS spectroscopy is to use the surface of small particles, with dimensions on the order of 1 to about 100 nanometers, as the SERS active media for analysis. These nanoparticles can produce large enhancements of the Raman scattering of an analyte when that analyte binds to the surface. The frequency at which one or several Raman bands is observed may be used to identify the chemical composition of the analyte and to distinguish it from other analytes that may bind to the SERS active surface. The intensity of the Raman band may be related to the amount of analyte present. The SERS effect has a very unique capability for detecting only species at or very near to the active surface. This means that properly constructed assays can proximally eliminate interferences from other species.

Ten to twenty years ago a SERS assay would most likely have been considered impractical because the instrumentation for Raman spectroscopy was very large, delicate, and expensive. Recent advances in optics, detectors, and lasers have made Raman systems small and compact enough for practical low-cost assays.

Modern methods of chemical analysis include wet chemistry, spectroscopy, chromatography, and electrochemistry. All of these methods vary in the amount of information that can be obtained in an analysis. For example, most electrochemical techniques measure current at a given applied potential. Such a technique would be considered poor in information content. Many simple spectroscopic measurements are also made by measuring an optical signal at a single wavelength. For example, ultraviolet or visible absorption spectroscopy is often performed with a low-cost instrument that illuminates the sample with a small band of wavelengths and the sample is quantitated using the linear relationship between the amount of light absorbed and the concentration. This too would constitute a technique that is poor in information content.

Cyanide analysis represents a good example of the problems with wet chemistry and electrochemical detection. Currently, the most popular method for cyanide measurement is a wet chemical method. It involves a dye that changes color when silver ions are present. Silver ions also react strongly with cyanide. The assay uses a solution with a known silver ion concentration to titrate an unknown sample of cyanide. After all silver ions in the known solution of silver ions have been complexed with cyanide, the presence of free silver ions is indicated by a color change due to the dye. This method can produce a fairly accurate analysis, but requires a significant amount of time to measure the cyanide concentration. Moreover, is highly subjective with regards to the color change, if performed by a person. It is also subject to severe interference from solutions that contain other species with complex with silver ions. Cyanide is electrochemically active and can be detected in pure solutions by electrochemistry. However, as electrochemistry is very sensitive to contamination and does not provide a distinguishing signal between cyanide and interferences, it is subject to error.

Also, in the case of cyanide, the desired quantity is often "free" cyanide. This is cyanide that is not bound to a metal. Free cyanide is most accurately measured by finding the "total" cyanide obtained by mixing the sample with a strong acid and collecting the evolved hydrogen cyanide gas in a sodium hydroxide solution and measuring the cyanide concentration in solution using the titration method described earlier. Next, a second measurement of the "wad" or weak acid dissociable cyanide is made by adding a weak acid to the sample and measuring the amount of free cyanide using the above titration method. The "free" cyanide in the sample is calculated by determining the difference between the total cyanide and the wad cyanide. The total procedure is very time consuming, labor intensive, and uses dangerous reagents.

Cyanide in blood is also very difficult to measure. It binds to the hemoglobin in the blood and is also present as "free" cyanide in the serum. A common method for measuring cyanide in blood is to add a strong acid to produce hydrogen cyanide and to detect the hydrogen cyanide with a gas chromatograph. Given that death from cyanide poisoning can occur within minutes, such an analysis is not practical for diagnosis.

As demonstrated above, current methods for measuring cyanide are time consuming and often require several steps to produce a meaningful value. For first responders, such as emergency medical technicians, a rapid cyanide analysis is needed. Moreover, in view of the recent concerns about chemical warfare, it would be even more advantageous to detect and prevent contact with cyanide before a blood analysis is needed.

Some modern methods of analysis are rich in information and provide rapid results. For example, spectroscopy based on molecular vibrations tend to produce data that is composed of a signal spread over a large range of wavelengths. This allows one to delineate the contribution of many analytes in the sample in a single spectrum. Two basic forms of vibrational spectroscopy exist: infrared absorption and Raman scattering. Infrared absorption spectroscopy measures the absorption of infrared radiation by molecules. The absorption occurs whenever the energy of the radiation matches the energy of a molecular vibration in the sample. Infrared absorption spectroscopy is rich in information, but can be difficult to use as an analytical tool. The infrared radiation is strongly absorbed by glass and other common optical materials. This requires the samples to be contained in materials like potassium bromide, which is very brittle and hard to shape into even the simplest sample container. This alone is a difficulty, but for quantitative analysis it is very difficult to control the thickness of the sample. If the thickness is unknown it is impossible to relate the absorbance to the concentration. Water is also a strong absorber of infrared radiation and interferes with analysis. This is particularly troublesome with aqueous samples.

Raman spectroscopy stems from the inelastic scattering of light by molecular vibrational energy levels. Also termed Normal Raman scattering, it is performed by exciting the sample with a strong optical source, usually a laser. The Raman scattered light is emitted from the sample and collected with an optical element, usually a lens. Once collected, the light is dispersed with a spectrometer and analyzed with an optical transducer. Raman spectroscopy, as an analytical tool, has been known for decades, and is particularly popular for several reasons. For example, molecular composition can be determined in the presence of water. Visible light can be employed for analysis allowing for the use of conventional optical materials. Unique spectral fingerprints allow for identification and quantification of a wide variety of solids, liquids, and gases. These advantages are overshadowed by an inherent lack of sensitivity of Raman scattering. This lack of sensitivity has precluded the use of Raman spectroscopy in application where low levels of material need to be detected, however SERS spectroscopy provides the means whereby it may be used in just such applications as described herein.

Surface enhanced Raman scattering (SERS) like many scientific discoveries, evolved out of serendipitous events. In the early 1970's, electrochemists began using optical methods to study electrode surfaces. Fleischmann and Hendra decided to experiment with Raman spectroscopy as a method of analyzing electrode surfaces. Due to the low sensitivity of Raman spectroscopy they chose silver as the electrode material since it is easily roughened by oxidation-reduction cycles in the presence of chloride. The growth of silver chloride crystals and reduction back to silver leads to a roughened surface with many times the surface area of a smooth polished electrode. This will increase the Raman signal, as there are more molecules in the laser beam. They chose pyridine as the probe molecule as it should adsorb through the pyridine nitrogen and it is an inherently strong Raman scatterer. Their experiment was a success. They did not know it, but this was the first experiment using SERS. It was not until four years later that this experiment was correctly interpreted. In 1977, Van Duyne at Northwestern University was also trying to study electrodes with Raman spectroscopy. His approach was to use resonantly enhanced molecular probes to overcome the sensitivity problem. Resonance Raman is an enhancement of Raman scattering achieved by exciting the molecule at a wavelength that matches an electronic absorption of the molecule. He had performed calculations to determine the amount of resonance enhancement needed to observe a monolayer on an electrode. This number was at least 1000 for a strong scatterer like pyridine. This made Flieschmann and Hendra's results look anomalous. To test if the enhancement was due to increased surface roughness, Van Duyne's student David Jeanmaire tried a milder oxidation-reduction cycle and achieved even stronger signals. This led to the first announcement of an anomalous phenomenon at silver surfaces.

It is now known that the SERS effect arises through an electromagnetic resonance that can occur strongly in noble metal particles and to a lesser extent in some other metals. The resonance occurs because the electrons in the particle are affected by the excitation light to produce a polarization in the particle that makes it more likely to become more polarized. This phenomenon will produce very large electric fields near the particle surface, thus amplifying optical events near the surface that are dependent on the electromagnetic field. Raman scattering is just one class of such events. Others might include fluorescence and absorbance.

While SERS was discovered on electrode surfaces, it is not limited to these. Today SERS is being performed on evaporated metal surfaces, etched metal foils, microlithographically produced surfaces, carefully assembled particle arrays, and colloidal suspensions. Other methods, capable of producing small submicron sized particles or features on a surface, also provide various SERS active surfaces.

Several problems have plagued the development of SERS into a practical analytical tool. One such problem is the delicate nature of the SERS substrate. The SERS phenomenon is associated with particles or roughness features that are about $1/10$ the size of the wavelength of the light used for excitation or about 40 to 100 nanometers. Particles of this size are very susceptible to chemical damage, aggregation, and photodamage.

A survey of the different SERS substrates produces one type that stands out with respect to practical analytical chemistry. These are colloidal suspensions. Two significant advantages are found with colloidal suspensions. First, a large volume of colloidal particles can be made at one time. Within this batch of colloids, every sample will be identical. This overcomes the irreproducibility of non-free floating particulate surfaces. The second advantage is that the colloidal particles are suspended in a solution and therefore tend to be much less susceptible to thermal damage. They also are subject to Brownian motion, which tends to continually refresh the particles in the excitation beam, thus eliminating problems with photodegradation of the sample.

Initially SERS was seen as advantageous because of its strong enhancement. This invention realizes a different aspect of SERS. The localization of the SERS enhancement near the surface very effectively separates the analyte that is in close proximity with the surface from analyte or other material in the sample matrix. The locality of the analyte can be used to a strong advantage with respect to the ease of analysis. SERS allows one to measure an analyte in the presence of species that would strongly interfere and cripple other methods of analysis that do not have a localized area of detection.

In addition to problems with SERS substrate stability and reproducibility, an additional factor needs to be included in the analysis. The SERS substrates are typically noble metal particles. The noble metals are aptly named for their ability to resist the aggressions of other materials. In a practical sense this is good for stability of the surfaces, but is impractical in terms of attracting an analyte to the surface. In order for the SERS substrate to act as a tool for detecting an analyte, it must attract the analyte to the surface or in some way be specifically affected by the analyte to show a spectroscopic response.

Small nanoparticles of gold and silver react with some chemical species to create a strongly bound surface complex.

This complex may be observed spectroscopically as a bound species. A condition for the observation of the bound species is the ability to distinguish between the surface-bound species and solution species or other interferences. This distinction often requires both a selectivity aspect related to the relationship between the energy of the light affected by the spectroscopic measurement and the intensity of the light affecting the spectroscopic measurement.

With respect to cyanide and related species, the noble metals gold and silver tend to form very strong complexes with these species. In solution or in the air, particles of silver or gold tend to bind cyanide very strongly to give a surface coating composed of metal cyanide complexes.

One example of a spectroscopic technique is Raman spectroscopy, which is very specific in its ability to measure between complexed and solution species or differences between cyanide species. Moreover, SERS is very surface specific, such that it can identify between solution and surface bound species.

The SERS phenomenon is electromagnetic and at times may also be due to the formation of a surface bound chemical species that is spectroscopically unique and distinguishes itself to provide an indication of the presence of the species. For example, the formation of a complex that has an electronic absorption may lend itself to detection through UV-Vis absorption spectroscopy, fluorescence, or resonance Raman spectroscopy.

Often both the electromagnetic enhancement and the additional chemical enhancement require the addition of special agents. These agents may change the morphology of the surface to produce a size or shape that is more conducive to the electromagnetic SERS effect or they may form mixed complexes with the analyte (cyanide or related species) to produce a product (complex) with a unique electronic absorption. The morphology of SERS active surfaces is crucial for large enhancements. A popular form of a SERS active medium is colloidal particles. These are spherical particles that tend to be so small that they do not aggregate or settle out of solution.

The advantage of colloidal particles is their stability due to lack of aggregation and resistance to settlement due to their small size and continual movement due to Brownian motion. This can also be a disadvantage with respect to SERS. SERS comes largely from the electromagnetic enhancement of light at the particle surfaces. However, this enhancement is strongly dependent on the shape and size of the particle. Spherical particles tend to enhance light at short wavelengths. This can be impractical as laser sources are more common and more intense at longer wavelengths. If the particles become ellipsoidal in shape they exhibit an enhancement at both short wavelengths and longer wavelengths. This arises from the long (long wavelength enhancement) axis and the short (short wavelength enhancement) axis. Furthermore, as the particles become larger, the enhancement is shifted to longer wavelengths.

Up until now, the of detection cyanide and species reactive toward SERS active surfaces has been though direct adsorption to the SERS active surface or through the formation of bonds to a surface bound coating. This is often a sacrificial situation with the actual material responsible for the SERS effect being consumed by the detection method. A more favorable detection method would be to provide a solution species that reacts with the cyanide or related species and then adsorbs to the SERS active surface. This creates a surface species that relates to the cyanide or related species, but it does not consume the SERS active material.

Sometimes a sample contains more than one species (interferers) that can react with an activated SERS surface. At low levels of interferers, it may be possible to spectroscopically distinguish between them and the analyte. However, the amount of surface area available for analysis is limited and the interferers may occupy all sites available for analyte binding. Another situation might be a reaction between the interferers and the activated SERS material to render the SERS active material inactive. In such cases, it may be possible to convert the analyte to a gas and detect it as an adsorbed gas on the activated SERS surface. In this type of analysis, the interferers are left in solution and cannot interact with the spatially separated SERS active surfaces. An example of this type of analysis would be samples containing cyanide and interferers such as thiocyanate or blood metabolites. The sample could be treated with a sufficiently strong acid to produce hydrogen cyanide, but not strong enough to produce volatile sulfur containing species. An accurate assay can be performed if the activated SERS surface is located a distance from the solution such that the hydrogen cyanide can adsorb to the surface, but not the interferers in solution.

SUMMARY OF THE INVENTION

The present invention includes a variety of aspects, which may be selected in different combinations based upon the particular application or needs to be addressed. One aspect of the invention is the use of additive or reagents to activate a surface to be reactive toward a chemical and/or a species related to the chemical. This aspect of this invention involves the addition of an activator to a surface or to a solution of nanoparticles to cause them to form a better shape or size for realizing strong surface enhancements.

Another aspect of the present invention is the addition of an activation agent, which based on the application, may lead to improved signals by means other than or in addition to shape or size improvement of nanoparticles for surface enhanced Raman assays. This aspect involves the use of an activating agent that, when present with a chemical and/or a species related to the chemical, produces a complex on the surface capable of surface enhanced Raman, which produces a noticeably stronger Raman signal.

Another aspect of the present invention is an agent to improve the assay of a chemical and/or a species related to the chemical. This aspect involves the addition of a material that stabilizes the surface with respect to surface enhancement. There are two subcategories of these stabilizing agents. First, there is a category of stabilizing agents that halt the activation process to keep the activation agents from changing the shape or size of nanoparticles so much that they no longer produce surface enhancement. Second, is a stabilizing agent that prevents the analyte from adversely affecting the size and shape of a surface capable of producing surface enhanced Raman scattering. Cyanide and related species fall into this class of analyte. This second category of stabilizing agents provides protection of the metal surface to prevent dissolution by the chemical and/or the species related to the chemical.

Yet another aspect of the present invention is the use of a sacrificial agent to prevent the metal surface, which is capable of surface enhancement, from being dissolved or adversely affected by the presence of a chemical and/or a species related to the chemical. For example, silver nitrate may be added to the assay to react with cyanide and/or a species related to cyanide before it can adversely affect the surfaces. In this case, the cyanide or related species that may be harmful to the surface has been converted into a silver complex that is harmless to the surface, yet produces a large signal when adsorbed to the surface.

A further aspect of the present invention is the production of a gaseous form of a chemical and/or a species related to the chemical to enable detection. This aspect of the invention addresses two difficulties that can occur with the assay for the chemical and/or the species related to the chemical. First, is the difficulty presented when the chemical and/or the species related to the chemical is weakly bound to another species in the sample. This difficulty may prevent the chemical and/or the species related to the chemical from coming into contact or binding with the surface capable of surface enhancement. This particular aspect of the assay involves the addition of a material that releases the chemical and/or the species related to the chemical into the gas phase where it can be detected with a surface capable of producing surface enhanced Raman scattering. Second, is the difficulty presented by interferences. In many samples, a species will be present that may bind to the surface capable of surface enhanced Raman scattering and prevent the chemical and/or the species related to the chemical from binding or coming in contact with the surface. The gaseous form of the chemical and/or the species related to the chemical produced according to this invention will separate the chemical and/or the species related to the chemical from the interfering species that are in the sample solution. This feature of the chemical and/or the species related to the chemical gas phase may also eliminate the possibility of interference due to other difficulties, such as fluorescence, in the sample.

Still, another aspect of the present invention is the use of a barrier between the sample and the surface capable of surface enhancement to allow the gaseous form of the analyte to interact with the surface while prohibiting the sample solution from interacting with the surface. In accordance with this aspect, a gas permeable barrier is utilized, which either mechanically, with size selection or chemically, with chemical selection, passes a gaseous form of the chemical and/or the species related to the chemical, but prevents the solution form of the sample from passing.

Still yet another aspect of the present invention is a kit capable of detecting a chemical and/or a species related to the chemical. The kit may include activation agents, stabilizing agents, agents to release the chemical and/or the species related to the chemical from a sample solution as a gaseous material, and a gas permeable barrier.

DETAILED DESCRIPTION OF THE INVENTION

Figure 1:
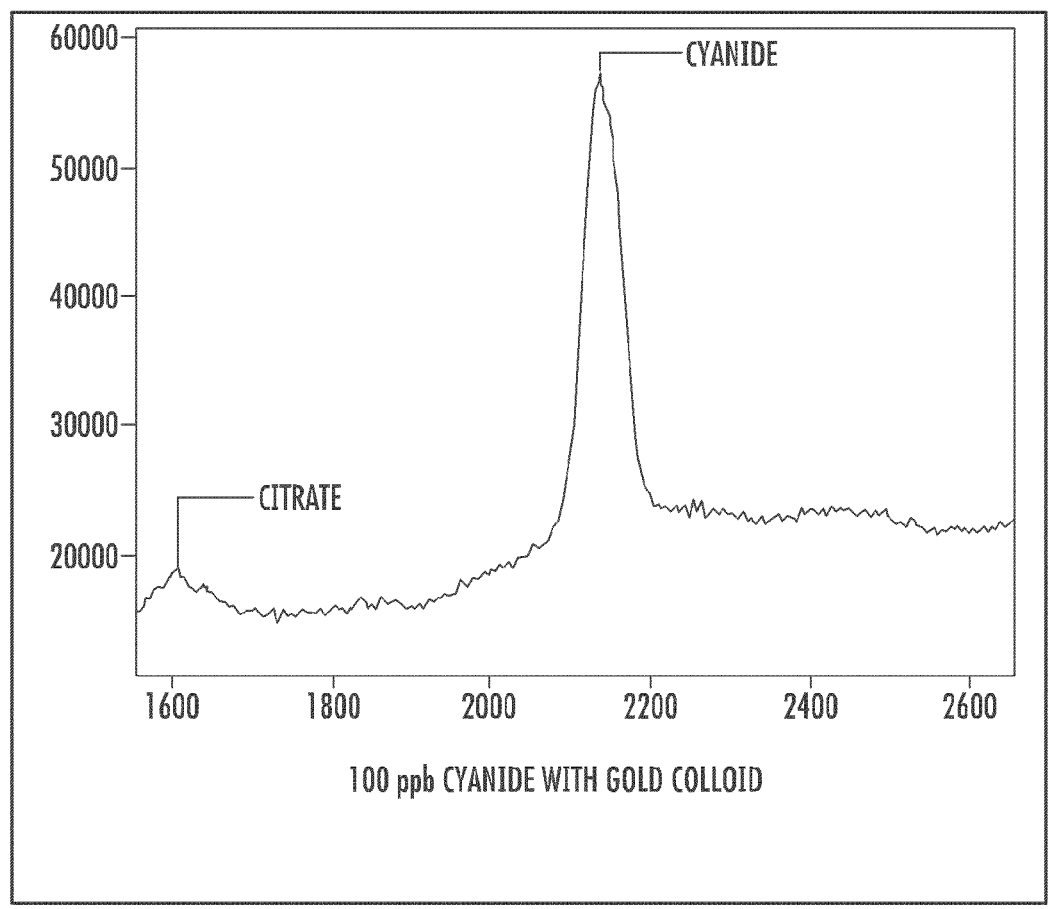
FIG. 1 is a surface enhanced Raman spectrum of cyanide adsorbed to a gold colloidal surface.

The present invention is an assay method and kit for detecting a chemical and/or a species related to the chemical (hereinafter chemical or the related species) using a metal surface that maintains or produces large enhancements of the Raman scattering (surface enhance Raman Scattering or SERS) when the chemical or the related species binds (adsorbed) to the metal surface. The present invention is especially useful for detecting cyanide and/or a species related to cyanide, and therefore, will be described as it relates to same. One of ordinary skill in the art will appreciate that the present invention may be useful for detecting other chemicals and/or their related species.

As is well known, cyanide exits in many forms. Accordingly, the term "cyanide," as used herein, may refer to the many forms of cyanide. One form of cyanide is free cyanide, which has an accepted meaning that refers to the anionic form of cyanide or in other words, $CN^-$. Another common form of cyanide is a weakly bound cyanide and metal ion complex. In some industries this form of cyanide is called Weak Acid Dissociable (WAD) cyanide, to denote its ability to be dissociated from the metal with a weak acid. Cyanide can also be bound very strongly to some metals. In this case, it is only dissociable with a strong acid. Yet another form of cyanide is hydrogen cyanide. Hydrogen cyanide is a gas, though it may exist as a gas dissolved in a liquid.

The phrase "related species," as used herein, refers to cyanide-like species that often exhibit properties similar to cyanide, with respect to the addition of silver or gold nanoparticles. For example, thiocyanate is similar to cyanide, but has an additional sulfur atom in its molecular formula. Its interaction with gold or silver nanoparticles is likewise very similar to cyanide. Another related species would be compounds that contain sulfur and which bind to silver in a similarly strong fashion. A practical, related species would be a mustard agent that could be used as a weapon of mass destruction and which contains a sulfur atom that can bind strongly to a silver or gold nanoparticle.

One aspect of the present invention is the use of nanoparticles as the SERS producing metal surface. As used herein, the term nanoparticles may refer to a single nanoparticle, an aggregate of nanoparticles, or roughness features on a surface that have a size and shape that produces enhanced Raman scattering. A nanoparticle may have a diametrical dimension between about 1 nanometer and about 1000 nanometers. The nanoparticles (or nanoparticle) may be in a solution, on a surface, or in a lyophilized form that can be reconstituted to provide a solution.

Nanoparticles are utilized in the present invention because they produce an enhanced SERS signal when cyanide and related species is adsorbed to the nanoparticle surface. The enhancement is generally believed to be an electromagnetic phenomenon related to the size, shape, and dielectric characteristics of the metal. A chemical enhancement is also believed to occur in cases where the adsorbate and the metal form a new species that has better Raman scattering signal than the adsorbate alone. The nanoparticles are preferably composed of silver, gold, or copper, or any combination thereof, because these metals produce the strongest enhancements. Of these three metals, silver and gold are most preferred as copper is less practical to use, due to its reactivity to oxygen. Although silver and gold metal are most preferred in the present invention, other metals that exhibit the SERS effect may be used. For example, alkali metals have been reported to produce strong SERS signals, but are generally impractical due to their very high chemical reactivity. Platinum has also been reported to produce a SERS effect, but it is currently, a weaker effect than that found for silver or gold.

The nanoparticles utilized in the present invention, may be produced by a wide variety of methods. For, example, the nanoparticles may be produced by reducing silver or gold ions in a solution to generate a clumping of silver or gold atoms. As the clumping or aggregation continues, the atoms grow into particles of the proper size (about 1 nanometer to about 1000 nanometers is diameter) and spherical or elliptical shape to produce the SERS effect.

The nanoparticles may be produced in a solution that contains a species that adsorbs to the surface of the nanoparticle to produce an electrostatic charge. The electrostatic charge on the nanoparticles prevents them from aggregating, thereby forming a colloidal suspension that has long term stability due to particle charging. This maintains the nanoparticles in solution for long or even indefinite periods for time. In one exemplary embodiment, a colloidal suspension of nanoparticles may be produced by reducing silver or gold ions with a reducing species, such as a citrate. The citrate plays a duel role, as it operates as the reducing agent and as the adsorbate that produces the charge on the nanoparticles. Typically, the metal ion solution and a citrate solution are mixed, stirred, and heated to cause the formation of the nanoparticles. The size of the nanoparticles can be controlled by the conditions of the reaction. These conditions may include heating time, temperature, degree of stirring, method of addition of the citrate to the solution, and reagent concentrations. In another embodiment, a colloidal suspension of silver nanoparticles may be produced using a very concentrated silver nitrate solution. The silver nanoparticles of the resulting colloidal suspension are likewise very concentrated. Such a colloidal suspension is especially suited for detecting forms of cyanide and related species that have the ability to dissolve the silver nanoparticles, as the high concentration of silver nanoparticles has more surface area to react with the cyanide and related species.

The nanoparticles may be produced by other methods including, without limitation, evaporation of metal to produce thin films that exhibit the SERS effect, and treatments to metal surfaces that produce a roughness that mimics the size and shape of a nanoparticle. In one embodiment, silver or gold may be evaporated onto a surface to produce a thin film formed by a plurality of nanoparticle islands on the surface. Likewise, the evaporation may be made onto a surface that, inherently or by microlithographic procedures, has a roughness that produces the SERS effect when it is coated with a metal film. Surface treatments that may be used to produce the SERS effect include, without limitation, roughening of a surface of the metal, e.g., silver, gold, by mechanical abrasion, chemical etching, or electrochemical treatments. A chemical etch which may be used includes nitric acid that etches away the portions of a surface of the metal to produce roughness features. An electrochemical treatment that may be used includes, for example, the oxidation of a surface of the metal followed by reduction with one or more cycles. The one or more oxidation-reduction cycles produce roughness features that exhibit large SERS signals. In a preferred embodiment, a solution containing chloride ions may be used as an oxidant during the one or more oxidation-reduction cycles. The chloride ions react with the metal surface to produce metal chloride (e.g., silver chloride, gold chloride) microcrystals on the metal surface. When the microcrystals are reduced back to the metallic state they tend to have dimensions of 1-1000 nanometers in diameter that are appropriate for the SERS effect.

A high concentration of cyanide may be detected in the present invention using a solution that contains a large quantity of nanoparticles. However, due to the dissolution of the nanoparticles by the cyanide, the mixture may be unstable. The mixture may be made stable by maintaining the cyanide concentration are a low level relative to the surface area of the nanoparticles. This may be accomplished in the present invention by increasing the quantity of nanoparticles in the test solution. This increases the surface area and reduces rate at which the cyanide can dissolve the nanoparticles. A preferred method for increasing the quantity of nanoparticles is to provide them a colloid form as a "strong" colloid. A strong colloid has a much higher nanoparticle concentration. It has been observed that the strong colloid can withstand more concentrated cyanide solutions.

In a less desirable embodiment, the problem of mixture stability with high concentrations cyanide, may be overcome by measuring the SERS signal rapidly enough to avoid significant signal changes due to the dissolution of the nanoparticles by the cyanide or follow the rate at which the SERS signal is lost and relate that to the concentration of the cyanide.

The strong colloid may be provided as an immobilized colloidal suspension. For example, the strong colloid may be provided as a lyophilized aliquot of nanoparticles. This method has the advantage that the lyophilized aliquot of colloidal nanoparticles may be reconstituted to give a SERS active colloidal solution. The reconstituting solution may include a sample to be tested. In addition, the colloidal suspension may take the form of simple evaporated solutions on a surface. They may also include surfaces that are reactive to the nanoparticles and have the ability to chemical adsorb the nanoparticles from a solution.

Figure 2:
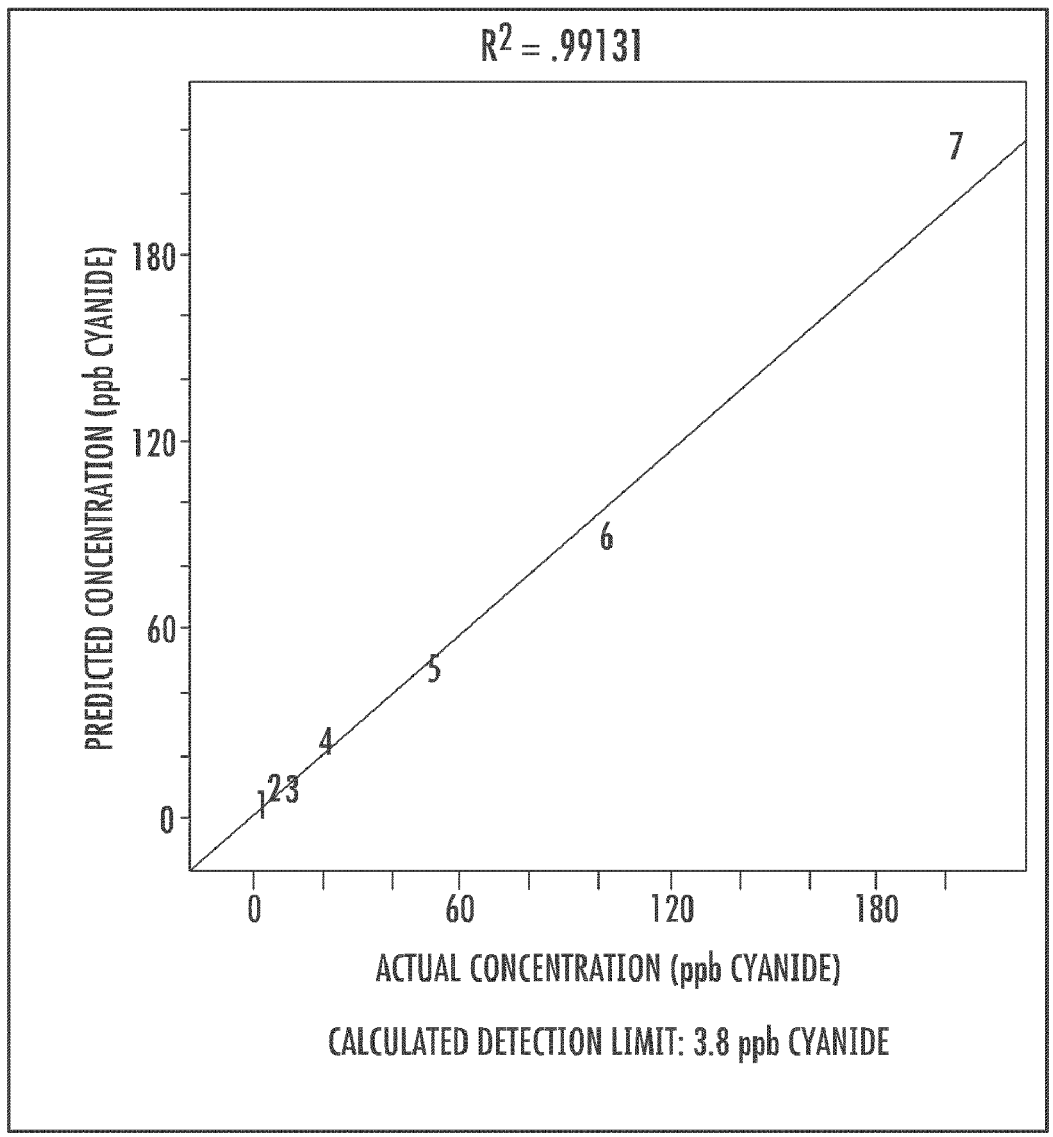
FIG. 2 is a plot showing the concentration of cyanide in solution as predicted by a model created from the surface enhanced Raman scattering intensity versus the actual concentration.
Figure 3:
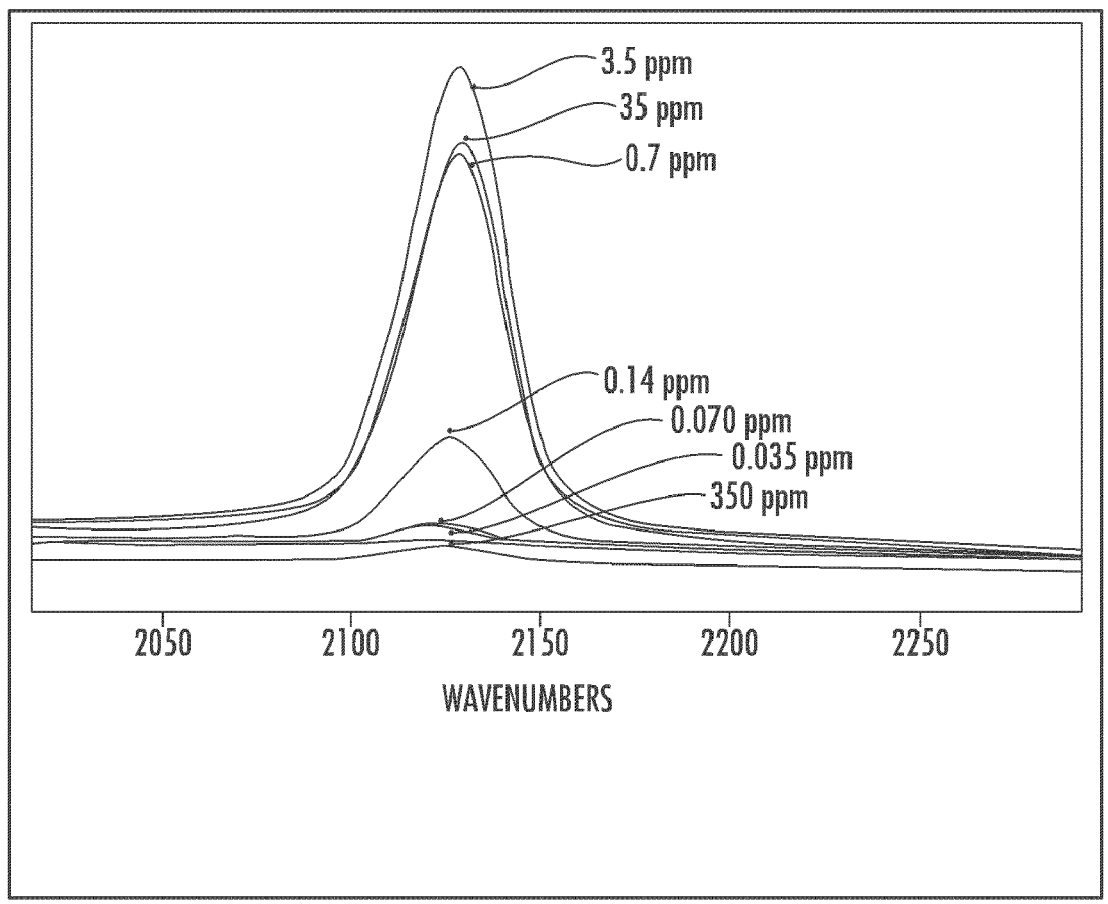
FIG. 3 is a plot of an overlay of surface enhanced Raman scattering spectra of cyanide on gold colloid.

The above discussion is supplemented by FIGS. 1-3. FIG. 1 shows a surface enhanced Raman spectrum of cyanide adsorbed to a gold nanoparticle surface. The solution concentration of the cyanide was 100 parts per billion.

FIG. 2 is a plot illustrating the concentration of cyanide in solution as predicted by a model created from the surface enhanced Raman scattering intensity versus the actual concentration. The $R^2$ value of 0.991 is indicative of an excellent correlation between the model predictions and the actual concentrations.

FIG. 3 is a plot illustrating an overlay of surface enhanced Raman scattering spectra of cyanide on gold nanoparticles which shows the relationship between intensity and concentration and illustrates the instability of an assay for cyanide over a large concentration range. These spectra span a very large range of concentrations. The highest concentration, 350 parts per million, produces the lowest signal. The highest signal is observed from an intermediate concentration of 3.5 parts per million.

In another embodiment of the present invention, the nanoparticles may be provided in solution form. In a solution containing silver or gold ions, it is known that cyanide prefers to bind to the silver or gold ions by 14 or more orders of magnitude. It is thought that the surface of a nanoparticle is likewise attractive to cyanide and will react with the same propensity as ions. There is evidence for this in the similarity between the spectroscopy of cyanide adsorbed to a nanoparticle surface and spectroscopy of the metal/cyanide complex. In this embodiment, the SERS effect is realized through cyanide's natural propensity to adsorb to metal nanoparticle surfaces. The SERS effect produces a very large spectroscopic signal due to the adsorbed cyanide or related species. When silver colloidal solutions are used, detection levels from high parts per billion to high parts per million are observed. Gold, which has a much higher affinity for cyanide, detects cyanide from the high part per trillion to low part per million level. This embodiment of the invention may be very useful when the sample is relatively clean and does not possess strongly interfering species.

In another aspect of the present invention, additives may be used to enhance the SERS signal. In one embodiment, an activating agent may be utilized to significantly enhance the SERS signal from a solution containing cyanide and a nanoparticle suspension. This is particularly useful when detection levels are needed to be very low. The activating agent may be an additive that causes an elongated aggregation of the nanoparticles. It is believed that the SERS signal from an elongated aggregation of nanoparticles will be larger than the SERS signal from a single nanoparticle. This has been explained by current theories that describe SERS as an electromagnetic effect that depends on the size and shape of the nanoparticles. This theory states that elliptical particles will produce larger enhancements. Two or more nanoparticles coupled in a chain would represent an elliptical particle.

Figure 4:
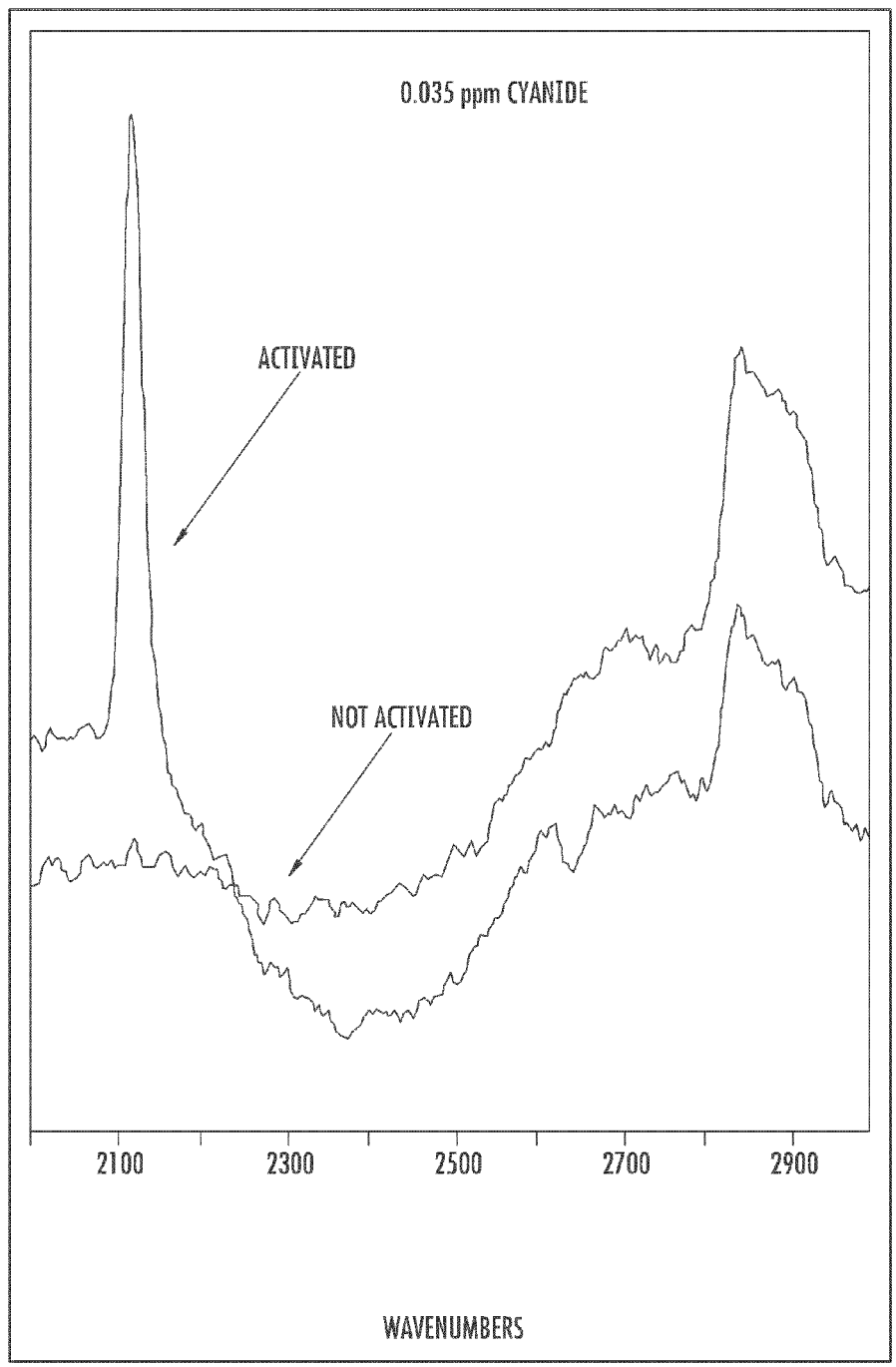
FIG. 4 is a plot illustrating the signal improvement with an activating agent.

FIG. 4 is a graph that illustrates the signal improvement with an activating agent additive. In this case the solution concentration of cyanide is 35 parts per billion. It can be seen that without the activating agent, sodium chloride, that no signal is observed for cyanide. However, upon addition of a small concentration of sodium chloride a very strong signal is observed.

The activating agent may also interact with the cyanide or related species on the surface of the metal nanoparticle to produce a larger surface enhancement. This has been observed when activating agent, such as chloride, increase signals from adsorbates on solid surfaces. Since the surface is not mobile and the formation of chains cannot occur, the signal increase cannot be due to morphological changes. In this case, it is believed that the activating agent is enhancing the SERS signal produced by the adsorbed species, not improving the enhancement produced by the nanoparticle. Chloride is only one example of an activating agent that may be used in the present invention to increase the SERS signal. Further activating agents that may be used in the present invention include, without limitation, other halides or species that cause nanoparticles to aggregate or which form complexes with cyanide and related species.

As discussed earlier, an activating agent may be used to enhance the SERS signal by coupling the nanoparticles together to produce a chain. This coupling is only beneficial to the extent that the nanoparticles stay in solution. As the chains get longer they tend to fall out of solution, thus reducing the SERS signal and causing the assay result to no longer be accurate. Thus, another additive that may be utilized in the present invention to enhance or prevent a loss in the SERS signal is a stabilizing agent, i.e., a material that prevents or at least reduces excessive aggregation of the nanoparticles or prevents a loss of the SERS signal due to sample interferences, such as salts which can adsorb to the nanoparticles and cause them to aggregate. In one embodiment, the stabilizing agent may be a surfactant, such as polyoxyethylene(10)isooctylphenylether, which is sold under the tradename Triton X. The polyoxyethylene(10)isooctylphenylether surfactant operates by binding to the nanoparticles and preventing their aggregation. Similar surfactants may also increase the viscosity of the solution and prevent or slow down the coupling of nanoparticles. This type of a stabilizing agent affects the nanoparticles.

Another type of a stabilizing agent that may be used as an additive in the present invention is an interactive stabilizing agent, i.e., a species that interacts with the cyanide or related species to prevent it from rendering the nanoparticles inactive. One example of an interactive stabilizing agent that may be utilized in the present invention is silver nitrate. In a nanoparticle solution, silver nitrate has no effect on the nanoparticles, but it will react with a cyanide or related species. With cyanide, silver nitrate reacts with at least two cyanides to produce a negatively charged metal complex. This complex has an affinity for the nanoparticle surface, but is not likely to render the surface inactive. The signal from the silver cyanide complex may be used to detect and/or quantitate cyanide in the solution. As one of ordinary skill in the art will appreciate, any metal that reacts with cyanide and its related species may be used in the present invention as the interactive stabilizing agent.

Another type of additive that may be utilized in the present invention to enhance the SERS signal is a sacrificial agent. If the solution contains a species that has a large affinity for the nanoparticles or in some way renders the nanoparticles inactive, the sacrificial agent may be used to remove that species. The sacrificial agent is, therefore, a material that will react with a species in the sample to prevent the same species from interfering with the nanoparticles. The interfering species may be silver or gold ions in solution that reacts with cyanide or a related species, thereby preventing the cyanide or related species from dissolving the nanoparticles. A common interfering species in a mining solution might be sulfide or other sulfur related species. The sulfide or other sulfur related species has a large affinity for the nanoparticles and will render them inactive. This can be prevented or reduced by the addition of a sacrificial agent, such as zinc ions, that have a very high affinity for sulfur species. The zinc preferentially removes the interfering species from solution. In some embodiments, the sacrificial agent may also act like an activating agent by reacting with the cyanide or related species and then adsorbing to the nanoparticle surface to produce a signal related to the presence and concentration of cyanide or a related species. For example, silver nitrate, described earlier as an activating agent, may be used to prevent large amounts of cyanide from rendering the nanoparticles inactive and therefore may be considered a sacrificial agent.

Figure 5A:
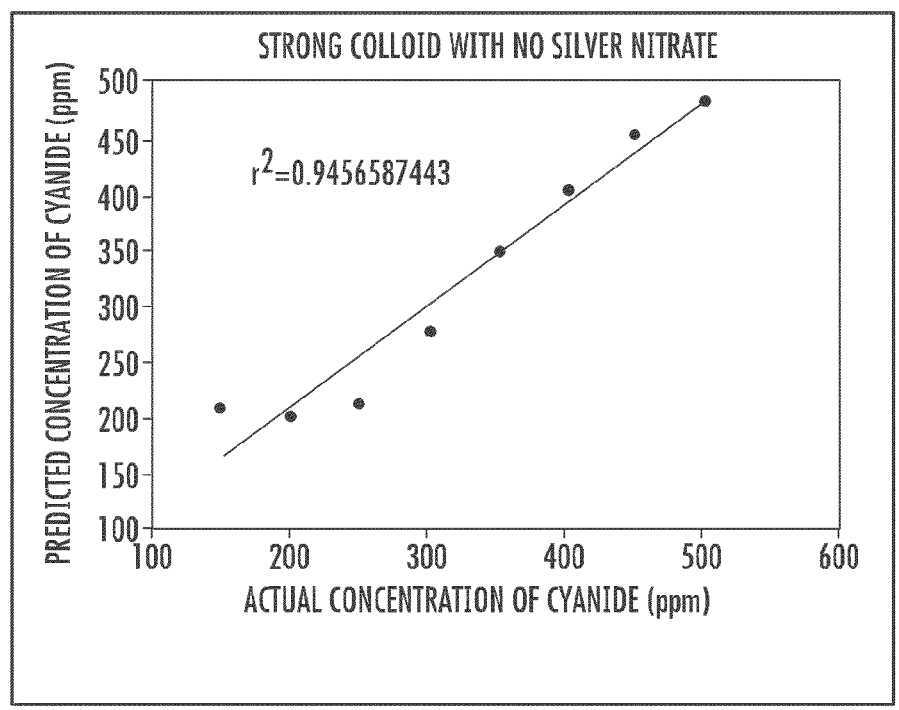
FIGS. 5A and 5B are plots illustrating the use of an activation/sacrificial agent.
Figure 5B:
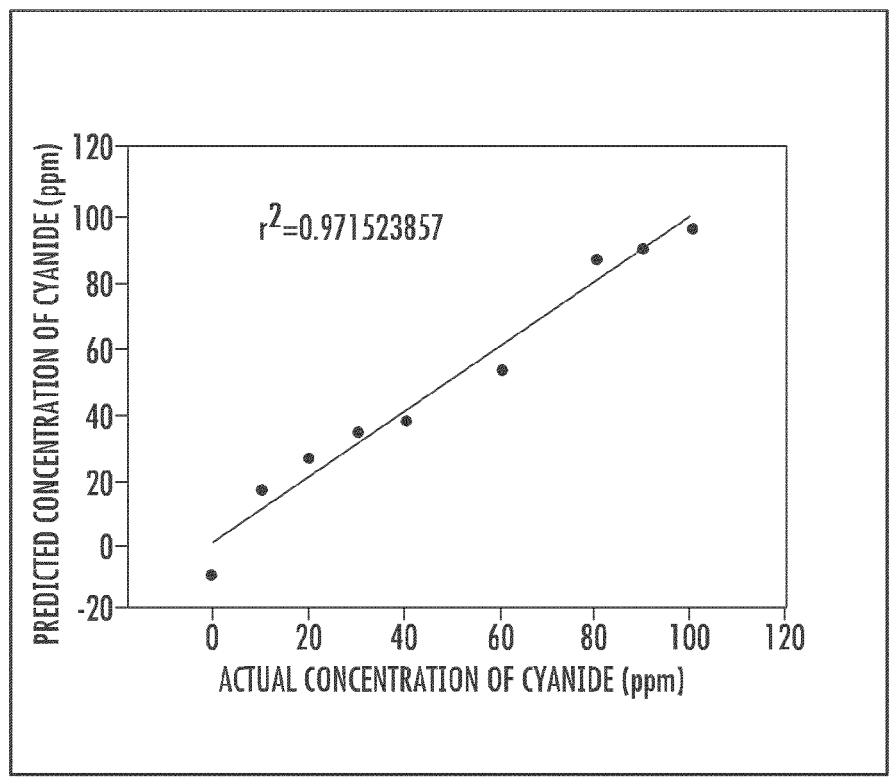

FIGS. 5A and 5B are plots illustrating the use of an activation/stabilization agent. In this case, the activating agent is silver nitrate. FIG. 5A is a plot showing the correlation between the model predictions and actual concentration of cyanide on a silver surface capable of surface enhancement. The concentrations are quite high, indicating that the silver surface has a lower affinity for cyanide and is less susceptible to dissolution. FIG. 5B is a plot showing the same silver surface in the presence of silver nitrate. In this case, the concentration range is much lower, due to the formation of a complex between the activator, silver ions, and cyanide. It was observed that the amount of silver nitrate could be adjusted to expand the range of detectable cyanide. In this case, the activator is both improving the signal and acting as a sacrificial agent by allowing it to react with cyanide before the cyanide can dissolve the silver surface capable of surface enhancement.

In yet another embodiment, the additive may be a releasing agent, such as an acid, that selectively converts the cyanide into a gaseous form, such as hydrogen cyanide, which is then detected after its removal or release from the solution. This is useful when the sample contains cyanide in a bound form or the solution contains interfering species. Several examples of this have been tested. One is the detection of WAD cyanide, which is a form of cyanide that is weakly bound to metal ions and can be released as hydrogen cyanide by a weak acid. In a solution that contains WAD cyanide it is possible to add a weak acid and collect the cyanide as a gaseous species on an immobilized nanoparticle surface or though a nanoparticle solution. Another application where the formation of gaseous hydrogen cyanide is useful is when the sample contains interfering species. For example, many mining solutions contain sulfur compounds. It is possible to make these solutions sufficiently acidic to remove the cyanide as hydrogen cyanide, but to leave the sulfur species in solution. Yet another example is cyanide in blood. When cyanide is in blood it binds to the iron in hemoglobin. This form of cyanide can be released as a gas by adding an acid to the blood solution and capturing the cyanide on an immobilized nanoparticle or a nanoparticle solution.

Another aspect of the present invention is a barrier that prevents the sample (a solution) or an interfering species from contacting the nanoparticles, which may be immobilized. This may achieved in one embodiment using a gas permeable membrane that allows gaseous forms of the cyanide or related species to pass through and bind with the nanoparticles, but prevents a solution and any interfering species in the solution from passing through and contacting the nanoparticles. Such a membrane may be made of a porous hydrophobic material, such as Teflon, that resists aqueous solutions, but allow gases, such as hydrogen cyanide, to pass though.

Figure 6:
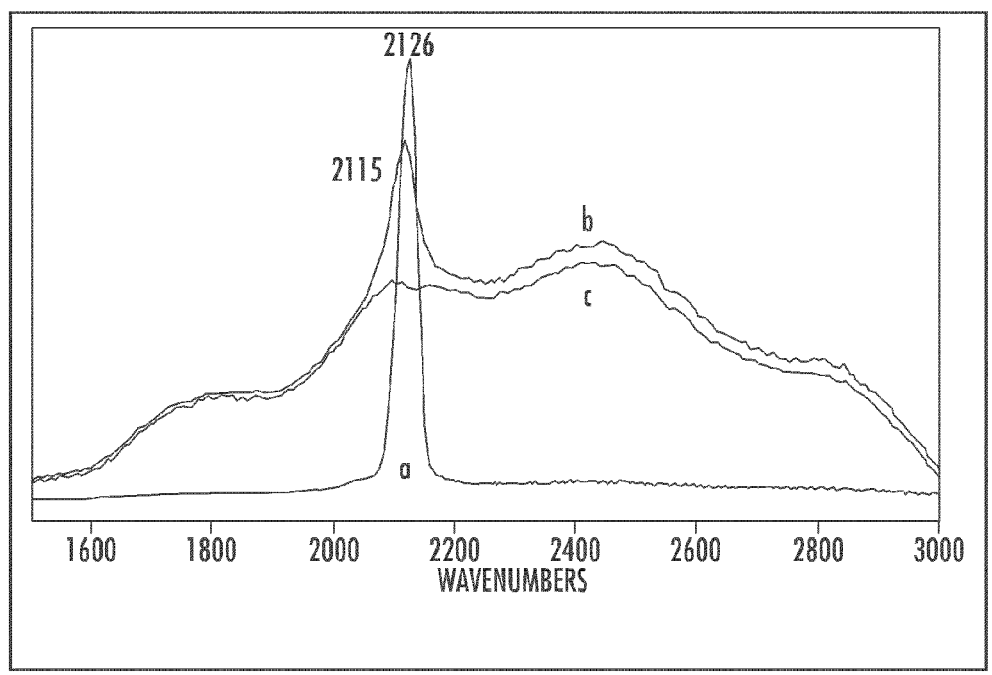
FIG. 6 is a plot illustrating an assay of cyanide with a gas permeable barrier and a releasing agent.

FIG. 6 is a plot showing an assay of cyanide using a Teflon barrier and a boric acid releasing agent. The boric acid causes cyanomethemoglobin to give up its cyanide as hydrogen cyanide gas. The hydrogen cyanide gas passes through the Teflon barrier, which has pores large enough to pass the hydrogen cyanide gas molecules, but is resistant to passing the solution. The surface capable of surface enhancement was comprised of gold nanoparticles deposited onto the Teflon membrane. Such an assay is especially useful for measuring cyanide in a patient's blood.

Figure 7:
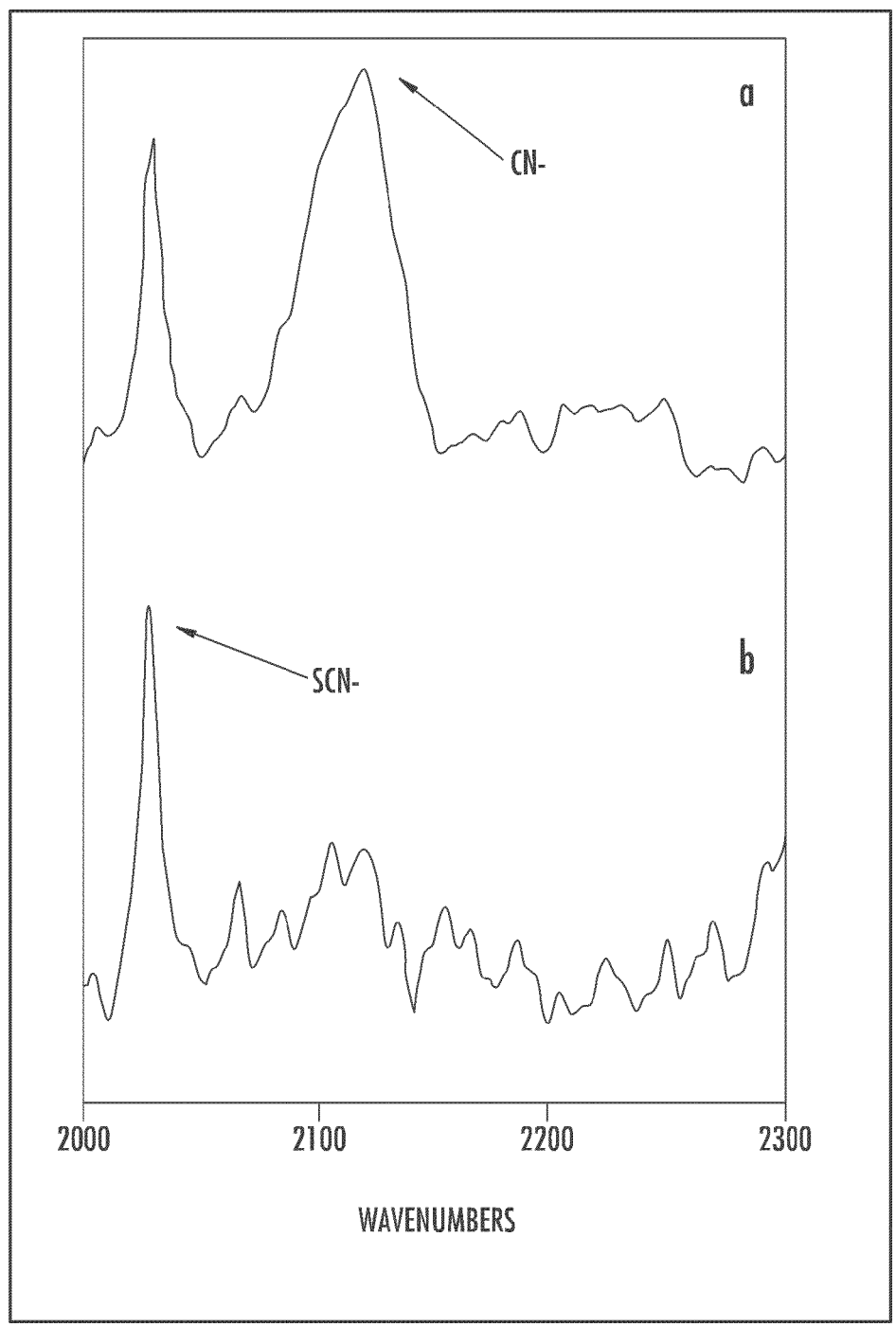
FIG. 7 is a plot illustrating the detection of cyanide in saliva.

FIG. 7 is a plot showing the use of the present invention to detect cyanide in saliva. The top spectrum is from the saliva of a cigarette smoker and shows cyanide and a related species, thiocyanate. The bottom spectrum is from the saliva of a nonsmoker and shows only thiocyanate.

Another aspect of the present invention is a kit for measuring the Raman signal from a sample. The kit comprises a combination of nanoparticles and additives (reagents) that when mixed with a sample cause the cyanide or related species to interact with the nanoparticles.

Figure 8:
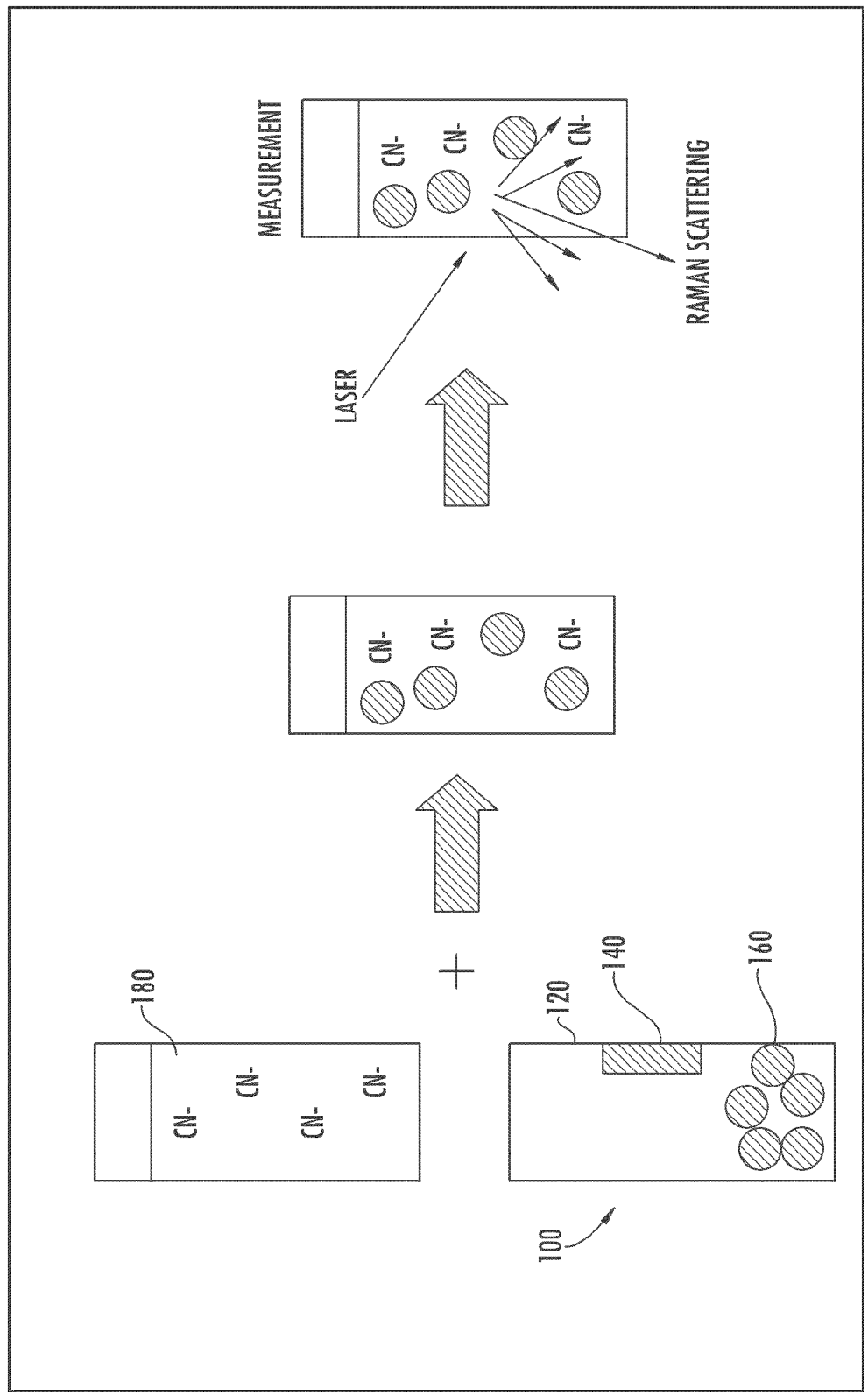
FIG. 8 is a diagram illustrating a first embodiment of a kit for a chemical and/or a species related to the chemical assay.

FIG. 8 illustrates a first embodiment of the kit 100 of the present invention for a cyanide assay. The kit 100 comprises a tube 120 containing one or more reagents 140 and metal (e.g., silver, gold) nanoparticles 160. The reagents 140 and nanoparticles 160 may be provided as a solution or desiccated. If desiccated, the reagents 140 and nanoparticles 160 will be reconstituted with a sample 180. Upon reconstitution or mixing of reagent 140 and nanoparticle 160 solutions with the sample 180, cyanide within the sample 180 will adhere to the nanoparticles 160. This binding event creates a solution that will exhibit very strong Raman scattering (SERS) that may be detected with instrumentation for Raman spectroscopy. The detected SERS signal may be used to determine the concentration of the cyanide.

Figure 9:
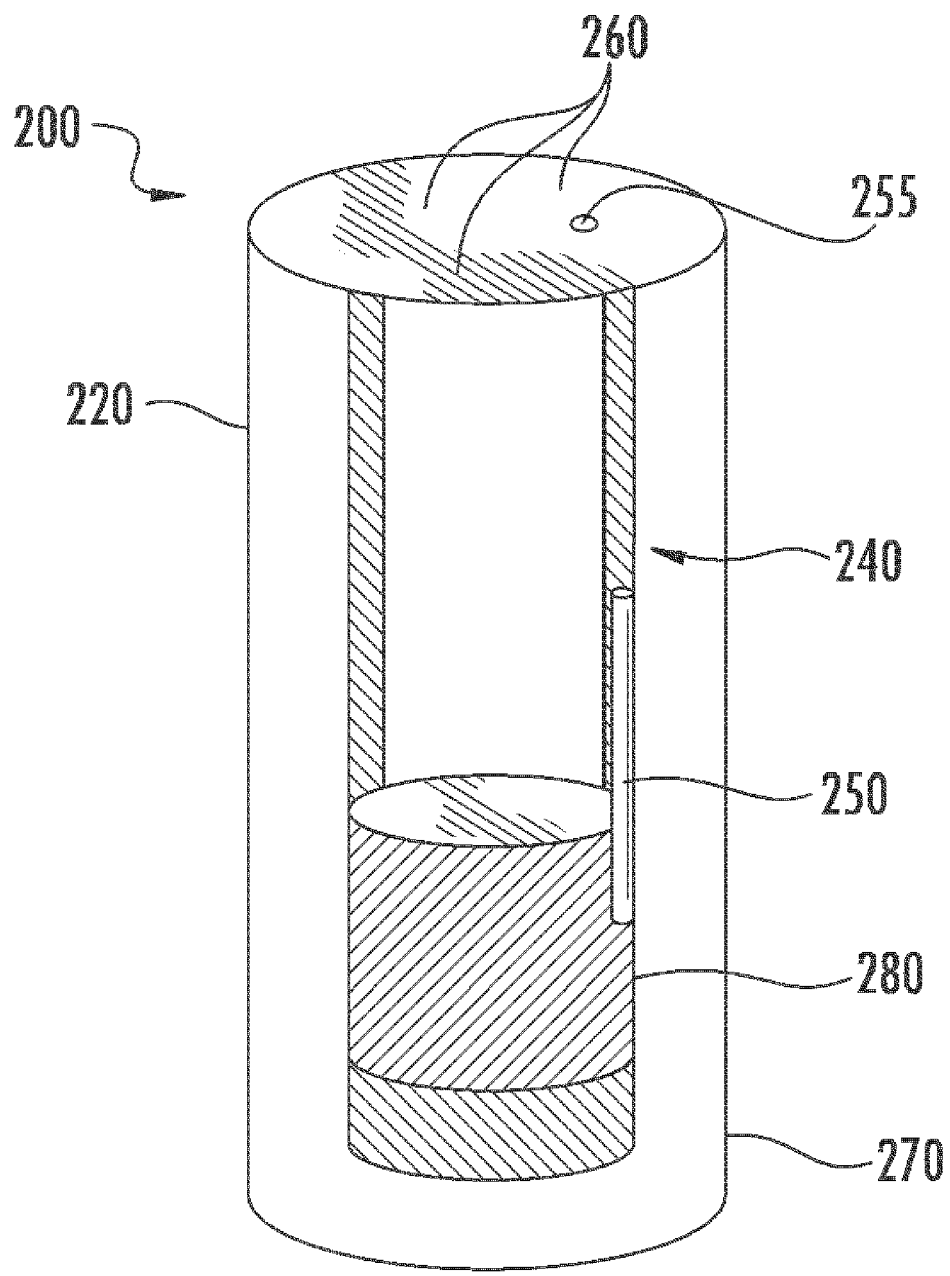
FIG. 9 is a diagram illustrating a second embodiment of a kit for a chemical and/or a species related to the chemical assay.

FIG. 9 illustrates a second embodiment of the kit of the present invention for a cyanide assay. The kit 200 is comprised of a tube 220 that contains a release agent 240, a stirring rod 250, and a gas permeable membrane 255 that is coated on the top surface with metal (e.g. silver, gold) nanoparticles 260. A sample 280 (e.g., blood) is placed in the tube 220, perhaps by capillary action, and sealed with a material 270, such as Critoseal. When the sample 280 is mixed with the releasing agent 240 the gaseous form of cyanide, hydrogen cyanide, is formed and passes through the membrane 255 and reacts with the metal particles 260. The assay is measured by acquiring a Raman spectrum from the cyanide adsorbed to the metal surface.

EXAMPLES

1a) Preparation of Silver Colloids: Silver colloids were prepared by a modified procedure of Lee and Meisel (P C Lee; D Meisel, J. Phys. Chem., 1982, 86, 3391). Silver nitrate (90 mg) was added to a 1000 mL Erlenmeyer flask containing 500 mL distilled water. While stirring this solution was heated to boiling. A 10 mL aliquot of an aqueous sodium citrate (1%) was added. Boiling and stirring were continued for 30 minutes, during which time the solution changed color from transparent gold to opaque yellow greenish color. The flash was removed from the heat source and the solution allowed to cool while stirring. The volume was adjusted with distilled water to makeup for fluid loss during the heating process, typically 100 mL. The colloid suspension was store in a Nalgene container at room temperature.

1b) Preparation of Strong Colloidal Silver: A mass of 0.800 g silver nitrate (99.999%) was dissolved in 0.800 L Millipore water contained in a specially cleaned Erlenmeyer 1 L flask. The solution was brought to a boil under rapid heating conditions and moderate stirring of approximately 100 rpm using a 50 mm Teflon stir bar. Upon boiling, a 25 cm thistle tube was inserted tightly in one hole of a 2-hole neoprene stopper having an enlarged second hole to vent excessive pressure. This apparatus was fitted on the flask, ensuring the thistle tube extended below the level of the solution. An aqueous sodium citrate solution (1% w/v) was freshly prepared from the dihydrate salt. Ten milliliter aliquots were added to the thistle tube and allowed to empty into the solution until an 88.9 mL volume of sodium citrate was dispensed. The thistle tube and stopper were removed and replaced with a watch glass. The solution was allowed to boil gently for an additional 1 hour with stirring. After the solution reached room temperature, the colloidal solution was vacuumed filtered through a 25 mm Whatman GFA filter. A 0.02 M solution of silver nitrate (19 mL) was added to the colloid, and the volume adjusted to 1 L. The strong colloidal solution was stored in an amber glass bottle until use.

1c) Preparation of Gold Colloids: Gold colloids were prepared by a modified procedure of Frens (G Frens, Natural Physical Science, 1973, 241, 20). An aqueous hydrogen tetrachloroaurate trihydrate solution (0.01%, 50 mL) was heated to boiling in an Erlenmeyer flask. To the gold chloride solution was added 0.20 mL of an aqueous sodium citrate solution (1%). Heating and stirring was continued for 40 minute during which time the solution changed color from clear to purple. Gold colloidal suspensions were stored in a brown Nalgene container at room temperature.

2a) Preparation of Potassium Cyanide Standards: Potassium cyanide standards were prepared by first making an aqueous stock solution of 1000 parts per million (ppm) potassium cyanide by dissolving 1 mg potassium cyanide in 1 mL distilled water. Less concentrated standards were prepared from this stock solution by diluting the appropriate aliquot of stock solution with distilled water for the desired concentration range.

2b) Preparation of Cyanide Standards: Cyanide standards were prepared by first making an aqueous stock solution of 1000 ppm cyanide by dissolving 1.89 mg potassium cyanide in 1 mL distilled water. Less concentrated standards were prepared from this stock solution by diluting the appropriate aliquot of stock solution with distilled water for the desired concentration range.

2c) Preparation of Cyanide Standards: Cyanide standards were prepared by first making an aqueous stock solution of sodium hydroxide (1.5%). The cyanide stock solution (1000 ppm) was prepared by dissolving 1.89 mg potassium cyanide in 1 mL of the sodium hydroxide (1.5%) stock solution. Less concentrated standards were prepared from this stock solution by diluting the appropriate aliquot of cyanide stock solution with aqueous sodium hydroxide (1.5%) for the desired concentration range.

2d) Preparation of Cyanide Standards: Cyanide standards were prepared by first making an aqueous stock solution of sodium bicarbonate (1%). The cyanide stock solution (1000 ppm) was prepared by dissolving 1.89 mg potassium cyanide in 1 mL of the sodium bicarbonate (1%) stock solution. Less concentrated standards were prepared from this stock solution by diluting the appropriate aliquot of cyanide stock solution with aqueous sodium bicarbonate (1%) for the desired concentration range.

3) Preparation of Acid Buffers: pH 2 buffer was prepared by dissolving one capsule of pre-measured pHydrion buffer (Metrepak) in 100 mL distilled. Capsule contains potassium biphthalate and sulphamic acid.

4) Preparation of Acid Solution: An acidic solution of pH 4.5 was prepared by dissolving 600 mg boric acid in 100 mL distilled water.

5) Sample Treatment with Modified Silver Colloid: In a 2 mL sample vial, 25 µL of sample was mixed with 50 µL of 3.27 M silver nitrate. The sample was vortexed for 5 seconds, followed by the immediate addition of 1 mL of strong silver colloid and mixed for an additional 5 seconds. A SERS spectrum was immediately acquired with an integration time of 10 seconds.

6a) Blood/Cyanide Assay in vials: To each 1.5 mL microcentrifuge tube was added 1 mL whole blood. This was followed by addition of 10 µL potassium cyanide/water standard, cyanide/water standard, cyanide/sodium hydroxide standard, or cyanide/sodium bicarbonate standard. For assay, 50 µL of blood/cyanide was added to 500 µL gold colloid in a 1 mL autosampler vial, mixed gently, and spectrum acquired with Raman instrument with a 1-30 second integration time.

6b) Saliva/Cyanide Assay in vials: To each 1.5 mL microcentrifuge tube was added 1 mL saliva. This was followed by addition of 10 µL potassium cyanide/water standard, cyanide/water standard, cyanide/sodium hydroxide standard, or cyanide/sodium bicarbonate standard. For assay, 50 µL of saliva/cyanide was added to 500 µL gold colloid in a 1 mL autosampler vial, mixed gently, and spectrum acquired with Raman instrument with a 1-30 second integration time.

7) Preparation of gold colloid coated gas permeable membrane: A PTFE gas permeable, hydrophobic membrane (GoreTex, WL Gore & Associates) and Millipore PTFE gas permeable, hydrophobic, 0.45 µL filters were used for fabrication of gold colloid coated membrane for HCN gas detection. The membranes were coated with 60 µL gold colloid suspension by desiccating aliquots (20 µL) of the colloid suspension onto the surface by drying under the heat of a desk lamp. The membrane was cut into 0.5×0.5 cm squares, each square containing 60 µL of desiccated gold colloid. The membrane squares were then affixed to the end of a blood collecting tube and stored in an airtight container at room temperature until use.

8) Fabrication of blood/cyanide and saliva/cyanide assay tubes: To each blood collecting tube was added 50 mL of pH 2 buffer or pH 4.5 boric acid solution. To each of these tubes was added a length (0.75 mm×0.5 cm) of wire rod, which will be used to mix the reagents after addition of the sample. The tubes were placed in an oven 100° C. overnight. Prepared tubes were returned to an airtight container and stored at room temperature until use.

9a) Blood/Cyanide Assay in blood collecting tubes: An assay consisted of drawing up sample, blood/cyanide standard, into the tube by capillary action. The open end of the tube was then sealed with Critoseal. A small magnet was used to move the wire rod through the tube thereby mixing the reagent with the sample. After 60 seconds of mixing the assay tube was placed in the sample holder of the Raman instrument and a spectrum acquired of the gold particles on the membrane. HCN gas is released by action of the reagent on the blood bound cyanide.

9b) Saliva/Cyanide Assay in blood collecting tubes: An assay consisted of drawing up sample, saliva/cyanide standard, into the tube by capillary action. The open end of the tube was then sealed with Critoseal. A small magnet was used to move the wire rod through the tube thereby mixing the reagent with the sample. After 60 seconds of mixing the assay tube was placed in the sample holder of the Raman instrument and a spectrum acquired of the gold particles on the membrane. HCN gas is released by action of the reagent on the cyanide containing saliva.

10a) Time Delay Experiments Before Recording SERS Spectra: The kinetic effects alter the SERS spectral intensity of a silver nitrate modified colloid solution, therefore, a two stage autopipettor was used to draw-up and deliver the reagents for assay. First, 700 µL of a stirring solution of silver nitrate modified colloid was drawn up, followed by an air space, then 70 µL of sample was drawn. The contents of the pipette tip were dispensed into a 1 mL glass vial. The Raman instrument was initiated within 1-2 seconds of the pipetting task and spectra acquired under a 5 second integration scheme. Sampling and data acquisition was repeated using 30, 60, 90, and 180 second wait times.

10b) Comparison of Silver Nitrate Reagent to Standard Titration Samples: An aliquot of 0.0200M silver nitrate solution (20 µL) was added to a mixture of 0.5 mL of silver colloid containing 20 µL of 50 ppm free cyanide. An enhanced SERS spectrum was observed in comparison to a SERS spectrum obtained by having no silver nitrate added.

While the foregoing invention has been described with reference to the above, various modifications and changes can be made without departing from the spirit of the invention. Accordingly, all such modifications and changes are considered to be within the scope of the appended claims.

What is claimed is:

1. A kit for detecting at least one of a chemical and a species related to the chemical, the kit comprising:
   a metal surface having at least one of a size and a shape that increases surface enhanced Raman scattering, the at least one of the chemical and the species related to the chemical adsorbing to the metal surface if exposed thereto; and
   at least one additive for at least one of: enhancing the surface enhanced Raman scattering due to the additive's affect on the metal surface; acting sacrificially to prevent the surface enhanced Raman scattering produced by the metal surface from being adversely affected by the at least one of the chemical and the species related to the chemical; and acting as an intermediate to react with the at least one of the chemical and the species related to the chemical prior to interaction with the metal surface.

2. The kit according to claim 1, wherein the at least one additive includes an activator that causes the metal surface to be more surface-enhanced-Raman reactive toward the at least one of the chemical and the species related to the chemical.

3. The kit according to claim 1, wherein the at least one additive includes a stabilizer that stabilizes the metal surface to maintain surface enhanced Raman scattering.

4. The kit according to claim 1, wherein the at least one additive includes a sacrificial agent to prevent the metal surface from being dissolved or adversely affected by the presence of the at least one of the chemical and the species related to the chemical.

5. The kit according to claim 1, wherein the at least one additive includes a material for releasing the at least one of the chemical and the species related to the chemical into a gas phase.

6. The kit according to claim 1, further comprising a barrier that prevents a liquid form of the at least one of the chemical and the species related to the chemical from contacting the metal surface but allows a gaseous form of the at least one of the chemical and the species related to the chemical to pass therethrough and contact the metal surface.

7. The kit according to claim 1, wherein the metal is silver.

8. The kit according to claim 1, wherein the metal is gold.

9. The kit according to claim 1, wherein the metal surface comprises at least one nanoparticle.

10. The kit according to claim 9, wherein the at least one nanoparticle is provided in one of a colloidal form and a solution form.

11. The kit according to claim 9, wherein the at least one nanoparticle is provided in a lyophilized colloidal form.

12. The kit according to claim 1, wherein the metal surface has a nanoparticle-like texture.

13. The kit according to claim 1, wherein the at least one of the chemical and the species related to the chemical is cyanide.

14. The kit according to claim 1, further comprising a container for storing the metal surface and the at least one additive.

15. The kit according to claim 1, further comprising a container for storing the metal surface and the at least one additive, and mixing the at least one additive with the metal surface and a sample to be tested for the existence of the at least one of the chemical and the species related to the chemical.

* * * * *